United States Patent
Huang et al.

(10) Patent No.: US 7,282,602 B2
(45) Date of Patent: Oct. 16, 2007

(54) MEDICINAL DISULFIDE SALTS

(75) Inventors: Qiuli Huang, San Antonio, TX (US); Harry Kochat, San Antonio, TX (US); Xinghai Chen, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 65 days.

(21) Appl. No.: 10/945,809

(22) Filed: Sep. 21, 2004

(65) Prior Publication Data

US 2006/0063949 A1  Mar. 23, 2006

(51) Int. Cl.
*C07C 309/00*  (2006.01)
(52) U.S. Cl. .................................... 562/103
(58) Field of Classification Search ............... 562/103
See application file for complete search history.

(56) References Cited

U.S. PATENT DOCUMENTS 5,661,188 A * 8/1997 Weissman et al. .......... 514/711

FOREIGN PATENT DOCUMENTS

EP  1152071 A1 * 11/2001

OTHER PUBLICATIONS

Brzezinska et al, Journal of Organic Chemistry, Disulfides. 1.Synthesis Using 2,2'-Dithiobis (benzothiazole), 1994, 59, p. 8239-8244.*

* cited by examiner

*Primary Examiner*—Paul A. Zucker
(74) *Attorney, Agent, or Firm*—Thomas J. Dodd; Scott A. Whitaker

(57) ABSTRACT

This invention relates to novel salts of medicinal disulfides. The compounds include a terminal sulfonate or phosphonate moiety, and have many uses, such as toxicity reducing agents when administered with many antineoplastic agents.

6 Claims, No Drawings

MEDICINAL DISULFIDE SALTS

FIELD OF THE INVENTION

This invention relates to novel salts of certain disulfide compounds. More specifically, the invention relates to pharmaceutical salts of dithio(alkane sulfonate) compounds that have use as protective agents for reducing the undesired toxic effects of certain drugs, as well as various other medicinal uses.

BACKGROUND OF THE INVENTION

Disodium 2,2'-dithiobis ethane sulfonate (dimesna; Tavocept®) is currently in Phase III clinical trials in the United States and abroad as a toxicity reducing agent useful in ameliorating the toxicity of cisplatin, paclitaxel and other antineoplastic agents.

Sodium 2-mercaptoethane sulfonate (mesna; Mesnex®; Uromitexan®) is an approved drug in the United States and elsewhere for reducing the toxicity of certain antineoplastic alkylating agents, and has been shown to be particularly useful in reducing the acrolein mediated toxicity of cyclophosphamide and ifosfamide.

To date, derivatives of mesna and dimesna have been synthesized in which the sulfonate groups have been replaced with phosphonate groups, and the length of the alkane chain has been modified. Other known derivatives of mesna and dimesna include hydroxylated derivatives as well as thioethers and other related compounds. Examples of such derivatives are disclosed in U.S. Pat. Nos. 6,160,167 and others.

Dimesna is the preferred drug for the reduction of the toxicity of platinum complex and other antineoplastic agents because of its stability in the less reactive disulfide form while in the slightly basic environment of the blood.

SUMMARY OF THE INVENTION

This invention provides for new and novel salts of dimesna having the following formula:

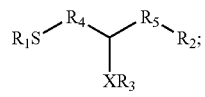

wherein $R_1$ is

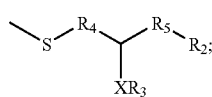

$R_2$ is $SO_3Y$;
$R_3$ is hydrogen or lower alkyl;
$R_4$ is $C_1$-$C_6$ alkylene or a bond;
$R_5$ is $C_1$-$C_6$ alkylene or a bond; and
X is oxygen or sulfur or X is a bond;
Y is selected from one of the group consisting of a group II metal ion; an L-amino acid residue; and an ammonium ion; or
pharmaceutically acceptable salts, prodrugs, conjugates, hydrates or polymorphs thereof.

The novel compounds of this invention will be useful as toxicity reducing agents when administered in combination with many classes of antineoplastic agents. In addition, the compounds will have use as therapeutic and/or palliative agents in the treatment of sickle cell disease, as antidotes for heavy metal poisoning, radiation exposure, free radical elimination, and many others.

This invention also provides for pharmaceutical formulations of the formula I compounds. The formulations include the formula I compound as active ingredient, along with one or more pharmaceutically acceptable excipients, diluents and/or solvents. The formulations may be prepared for either oral or parenteral administration to the patient.

Accordingly, it is a principle object of this invention to provide for novel medicinally useful compounds that have pharmaceutical applications in one or more therapeutic fields.

Other objects will become apparent upon reading the following specification.

DESCRIPTION OF THE PREFERRED EMBODIMENTS

The preferred embodiments herein described are not intended to be exhaustive or to limit the invention to the precise forms disclosed. The are chosen and described to explain the principles of the invention, and its application and practical use to best enable others skilled in the art to follow its teachings.

For purposes of this invention, $C_1$-$C_6$ alkylene means a bridging moiety formed of as few as 1 and as many as 6 —$CH_2$— groups;

The compounds of this invention are novel disulfide salts, and have the following general formula I:

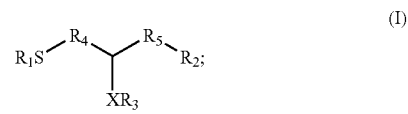

wherein $R_1$ is

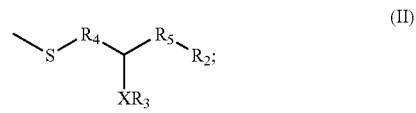

$R_2$ is $SO_3Y$;
$R_3$ is hydrogen or lower alkyl;
$R_4$ is $C_1$-$C_6$ alkylene or a bond;
$R_5$ is $C_1$-$C_6$ alkylene or a bond; and
X is oxygen or sulfur or X is a bond;
Y is selected from one of the group consisting of a group II metal ion; an L-amino acid residue; and an ammonium ion; or
pharmaceutically acceptable salts, prodrugs, conjugates, hydrates, solvates or polymorphs thereof.

Preferred compounds of this invention include those where Y is calcium or magnesium; L-lysine, L-arginine or L-glutamate; or ammonium ion. The compounds of formula I are synthesized by the following preferred process:

Scheme I

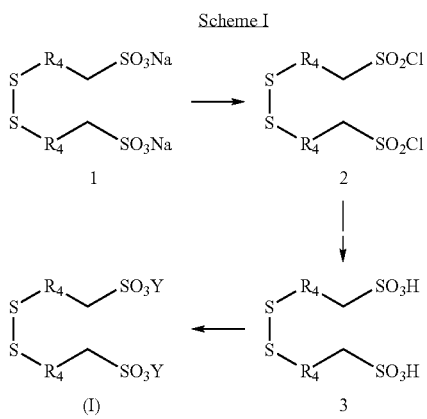

Other compounds falling within the scope of Formula I, i.e., those compounds having a longer alkylene chain or a hydroxyl or alkoxy moiety, may be synthesized using slight variations of the above Scheme I. As shown in Scheme I, the formula I compounds are preferably synthesized using dimesna (disodium 2,2'-dithiobis ethane sulfonate) as a starting ingredient.

Dimesna 1 is first converted to the disulfonyl chloride intermediate 2 through a known process utilizing sulfonyl chloride. Since the resulting thionyl chloride is highly lipophilic, an organic solvent may be used to extract the intermediate 2 from the reaction vessel. Intermediate 2 is then hydrolyzed to form the free sulfonic acid 3 of dimesna. A substitution reaction is then performed on acid 3 to form the compounds of formula I.

The formula I compounds are novel salts of dimesna 1, which has been shown to safely reduce the neurotoxicity associated with various taxane and platinum agents, as well as reducing the nephrotoxicity associated with cisplatin. Both dimesna 1 and the novel formula I salts are also predicted to be efficacious in detoxifying other platinum complex agents, as well as many other antineoplastic drugs. The compounds of formula I will also have usefulness against a variety of other conditions, such as heavy metal poisoning, radiation poisoning, sickle cell disease, and many others where free radicals are commonly present.

The following Examples illustrate the preferred synthesis of the some formula I compounds. The examples are in no way limiting of the invention or the process used to synthesize the formula I compounds. They are set forth to illustrate one of the preferred routes of synthesis.

EXAMPLE 1

Preparation of 2,2'-Dithiobis Ethane Sulfonyl Chloride

Dimesna (19.5 g, 60 mmol) in an ice bath was charged into a reaction flask followed by dropwise addition of thionyl chloride (30 mL, 0.41 mol). The reaction was catalyzed by adding small amounts of dimethyl formamide (0.8 mL). The reaction mixture was stirred at room temperature for three days. The mixture slowly developed into a homogeneous viscous solution. The excess thionyl chloride was removed by distillation. Dichloromethane (3×60 mL) was added to extract the product. The dichloromethane extractions were combined and concentrated until about 20 mL of liquid solution remained. The product was slowly crystallized and precipitated from the dichloromethane solution to afford 14.9 g (78% yield) of substantially white crystals. 2,2'-Dithiobis ethane sulfonyl chloride was further purified by recrystallization from dichloromethane.

$^1$H NMR (CDCl$_3$, 300 MHz): 3.26 (m, 4H), 4.06 (m, 4H).
$^{13}$C NMR (CDCl$_3$, 75 MHz): 30.7, 63.9.
Elemental Analysis: Calcd. for C$_4$H$_8$Cl$_2$O$_4$S$_4$: C, 15.05; H, 2.53. Found: C, 15.13; H, 2.56.

EXAMPLE 2

Preparation of 2,2'-Dithiobis Ethane Sulfonic Acid 2,2'-Dithiobis ethane sulfonyl chloride (15.0 g, 47 mmol) was dissolved in a mixed solution of acetonitrile (100 mL) and water (30 mL). The reaction solution was stirred at room temperature for five days until no more sulfonyl chloride was detected. The reaction solution was then concentrated by rotary evaporation at elevated temperature to remove the volatile acetonitrile solvent and as much water as possible. The remaining aqueous solution was washed with dichloromethane (2×50 mL) and dried under high vacuum to give 12.7 g of disulfonic acid (96% yield). The product existed as a semi-solid form and was highly hygroscopic. It readily turned to a viscous liquid once exposed to air. No significant impurity was detected in the product by either NMR or HPLC.

$^1$H NMR (CDCl$_3$, 300 MHz) 2.79 (m, 4H), 3.03 (m, 4H).
$^{13}$C NMR (CDCl$_3$, 75 MHz) 28.4, 47.1. Mass: Calcd for C$_4$H$_{10}$O$_6$S$_4$: 282, Found: 281 (M-H).

EXAMPLE 3

Preparation of Calcium 2,2'-Dithiobis Ethane Sulfonate

A solution of 2,2'-dithiobis ethane sulfonic acid (2.5 g, containing 9% water, 8.1 mmol) in water (1.0 mL) was titrated with calcium hydroxide (98+% purity, Acros Organics) aqueous solution until the pH of the reaction solution was adjusted to 7.0. Overall, 0.60 g (8.1 mmol) calcium hydroxide was used. Acetone (200 mL) was added to the reaction solution to precipitate the product. The resulting white solid was isolated by filtration and dried under high vacuum to give 2.20 g of product (85% yield). The purity of the product was 97.4% from HPLC analysis.

$^1$H NMR (CDCl$_3$, 300 MHz) 3.03 (m, 4H), 3.28 (m, 4H).
$^{13}$C NMR (CDCl$_3$, 75 MHz) 31.7, 50.5.

EXAMPLE 4

Preparation of Diammonium 2,2'-Dithiobis Ethane Sulfonate

A solution of 2,2'-dithiobis ethane sulfonic acid (2.5 g, containing 9% water, 8.1 mmol) in water (1.0 mL) was titrated with ammonium hydroxide aqueous solution (28-30% concentration, Aldrich) until the pH of the reaction solution was adjusted to 7.0. Overall 2.6 mL of ammonium hydroxide was used. Acetone (200 mL) was added to the reaction solution to precipitate the product. The resulting white solid was isolated by filtration and dried under high vacuum to give 2.10 g of product (82% yield). The purity of the product was 98.2% from HPLC analysis.

$^1$H NMR (CDCl$_3$, 300 MHz) 3.04 (m, 4H), 3.28 (m, 4H).
$^{13}$C NMR (CDCl$_3$, 75 MHz) 31.7, 50.5.

EXAMPLE 5

Preparation of di-(L-lysine) 2,2'-Dithiobis Ethane Sulfonate

A solution of 2,2'-dithiobis ethane sulfonic acid (2.5 g, containing 9% water, 8.1 mmol) in water (1.0 mL) was titrated with L-lysine (97% purity, Aldrich) aqueous solution until the pH of the reaction solution was adjusted to 7.0. Overall 2.34 g of L-lysine was used. Acetone (200 mL) was added to the reaction solution to precipitate the product. The resulting white solid was isolated by filtration and dried under high vacuum to give 4.20 g of product (91% yield). The purity of the product was 96.2% from HPLC analysis.

$^1$H NMR (CDCl$_3$, 300 MHz) 1.43 (m, 4H), 1.67 (m, 4H), 1.86 (m, 4H), 3.00 (m, 8H), 3.25 (m, 4H), 3.70 (m, 2H). $^{13}$C NMR (CDCl$_3$, 75 MHz) 21.4, 26.4, 29.8, 31.8, 39.0, 50.5, 54.4, 174.6.

EXAMPLE 6

Preparation of di-(L-arginine) 2,2'-Dithiobis Ethane Sulfonate

A solution of 2,2'-dithiobis ethane sulfonic acid (2.5 g, containing 9% water, 8.1 mmol) in water (1.0 mL) was titrated with L-Arginine (98% purity, Aldrich) aqueous solution until the pH of the reaction solution was adjusted to 7.0. Overall 2.80 g of L-arginine was used. Acetone was added to precipitate the product. The product in aqueous solution was dried under high vacuum to remove as much water as possible. The residue was resuspended in ethanol (30 mL). The white precipitate was isolated by filtration, washed with ethanol (2×30 mL), dried to give 4.93 g of product (97% yield). The purity of the product was 96.3% from HPLC analysis.

The formula I compounds may be administered in any convenient dosage form, with the preferred formulations adapted for oral (PO) or intravenous (IV) administration. Since the water solubility of the compounds exceeds 200 mg/mL, formulations are not anticipated to be difficult to make. Further, the formula I compounds have proven to be of very low toxicity, similar to dimesna, which is less toxic than common table salt (Dimesna has not caused a single death in vivo, even at amounts exceeding 5000 mg/kg IV).

Preferred oral formulations include tablets and gelatin capsules, containing an effective amount of the formula I compound, while parenteral formulations are dissolved completely in distilled water prior to administration. Preferred dosage amounts will depend upon the purpose of the administration, with the usual recommended dose ranging from 10 mg/kg to 1,000 mg/kg.

The above description is provide for illustrative purposes only, and is in no way limiting of the invention, whose scope is defined by the following claims.

What is claimed is:

1. A compound having the formula I:

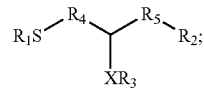

wherein R$^1$ is

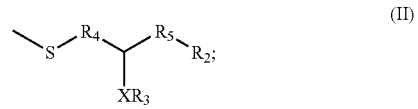

R$_2$ is —SO$_3$Y;
R$_3$ is hydrogen or lower alkyl;
R$_4$ is C$_1$-C$_6$ alkylene or a bond;
R$_5$ is C$_1$-C$_6$ alkylene or a bond; and
X is oxygen or sulfur or X is a bond;
Y is selected from one of the group consisting of a group II metal ion selected from the group consisting of beryllium, magnesium, calcium, strontium, barium, and zinc; an
L-amino acid residue; and an ammonium ion; or
pharmaceutically acceptable salts, prodrugs, conjugates, hydrates, solvates or polymorphs thereof.

2. The compound of claim 1, wherein in the formula of the compound:
R$_2$ is —SO$_3$Y;
R$_3$ is hydrogen;
R$_4$ is (—CR$_2$—)$_2$;
R$_5$ is (—CH$_2$—)$_2$; and
X is sulfur;
Y is selected from one of the group consisting of a group II metal ion selected from the group consisting of beryllium, magnesium, calcium, strontium, barium, and zinc; an
L-amino acid residue; and an ammonium ion; or
pharmaceutically acceptable salts, prodrugs, conjugates, hydrates, solvates or polymorphs thereof.

3. The compound of claim 1, wherein Y is calcium or magnesium.

4. The compound of claim 1, wherein Y is an L-amino acid residue selected from the group consisting of L-arginine, L-lysine and L-glutamate, or a pharmaceutically acceptable salt thereof.

5. The compound of claim 1, wherein Y is an L-amino acid residue selected from the group consisting of L-lysine and L-glutamate, or a pharmaceutically acceptable salt thereof.

6. The compound of claim 1, wherein Y is an ammonium ion.

* * * * *